United States Patent [19]

Matousek et al.

[11] 4,201,469

[45] May 6, 1980

[54] AEROSOL DEPOSITION IN FURNACE ATOMIZATION

[75] Inventors: Jaroslav P. Matousek, Forrestville; Lloyd E. Smythe, Belbue Hill, both of Australia

[73] Assignee: Unisearch Limited, Kensington, Australia

[21] Appl. No.: 821,148

[22] Filed: Aug. 2, 1977

[30] Foreign Application Priority Data

Aug. 2, 1976 [AU] Australia .............................. 6842/76

[51] Int. Cl.² .......................... G01N 1/00; G01J 3/30
[52] U.S. Cl. ........................................ 356/36; 356/312
[58] Field of Search ............................ 356/36, 85, 312

[56] References Cited

U.S. PATENT DOCUMENTS

| | | | |
|---|---|---|---|
| 3,736,059 | 5/1973 | Schuhknecht et al. | 356/36 X |
| 3,788,752 | 1/1974 | Slavin et al. | 356/85 |
| 3,893,769 | 7/1975 | Woolley | 356/85 |

OTHER PUBLICATIONS

"Continuous Sample Introduction with Ghathite Atomization Systems for Atomic Absorption Spectrometry," Kantor et al., Analytical Chemistry, vol. 46, #14, pp. 2205-2213, Dec. 1974.

*Primary Examiner*—Vincent P. McGraw

[57] ABSTRACT

A novel approach to sample deposition in furnace atomization is disclosed which obviates the need for skilled application of microvolumes by syringe. By means of the apparatus and method disclosed, the analyte in aerosol form is deposited under controlled conditions on the internal surface areas of graphite furnaces. Precision approaching that of flame atomization systems is achieved and at the same time, concentrational sensitivity may be increased simply by extending the deposition time. The amount of analyte deposited in the furnace is restricted only by the sample volume available and the matrix concentration. A single standard can be used to construct a calibration curve by simply varying the aerosol deposition time.

12 Claims, 5 Drawing Figures

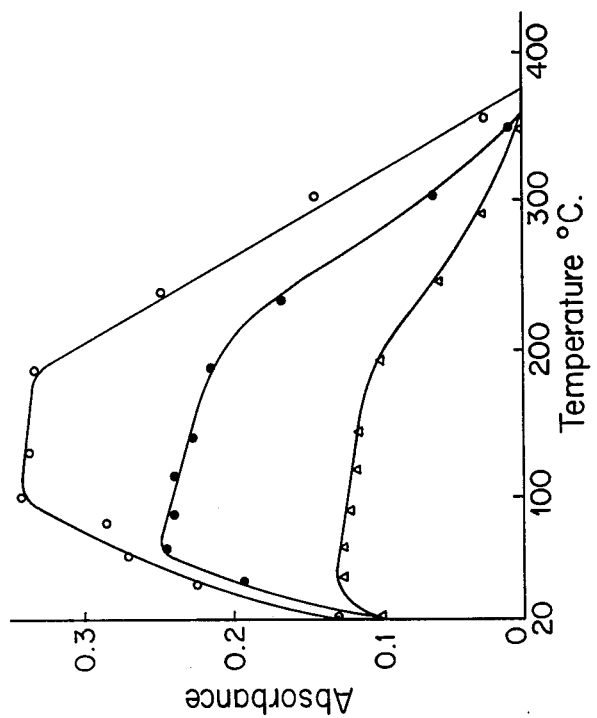
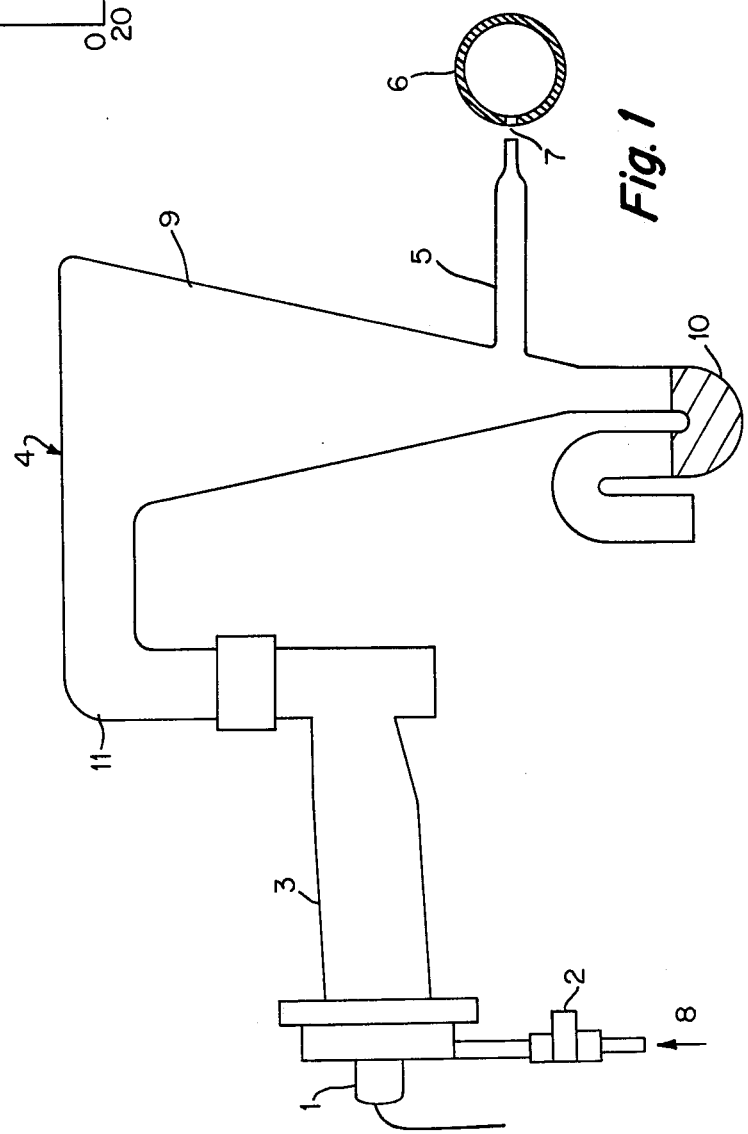

AEROSOL DEPOSITION IN FURNACE ATOMIZATION

The present invention relates to a method and to an apparatus for deposition of sample aerosol under controlled conditions inside furnaces used in atomic absorption, atomic fluorescence or atomic emission spectroscopy.

In recent years, atomic spectrometry, especially atomic absorption spectrometry, has found wide acceptance in industry and research establishments because of demands from such areas for methods of analysis of ever increasing sensitivity. Concern over such matters as the pollution of the environment and the function of trace metals in biological systems has resulted in the development of methods and apparatus capable of accurately determining minute amounts of elements. Details of the types, uses and advantages of various furnace atomizers are described in the review by Augusta Syty, "Developments in Methods of Sample Injection and Atomization in Atomic Spectrometry," CRC Critical Reviews in Analytical Chemistry, 4 (2), 155 (1974).

Flame emission, absorption, and fluorescence spectrometric methods of analysis depend primarily on the presence of analyte atoms in the flame. The atomic vapour is usually produced through a series of steps in which the sample solution is nebulized into an aerosol dispersion of small droplets, the droplets introduced into a flame, the solvent evaporated from the droplets to produce minute salt or oxide particles, and the particles converted into atomic vapour.

For more efficient conversion of the analyte element into atomic vapour, furnace atomizers were developed. Furnace atomizers require only a few microliters of sample per injection, whereas much larger volumes of solution must be available for analysis by flame. However, flame spectrometry is characterized by very reproducible measurements which has not always been the case with furnace atomizers.

The first successful furnace atomizer was described by Lvov (Spectrochim Acta 17, 761, (1961)) and its impressive sensitivity and novel design have inspired much of the recent wide interest and activity in the area of furnace atomizers.

Furnace atomizers commonly employ discrete samples and pulse atomization, rather than continuous sample introduction. It is the ability of these atomizers to cause efficient atomization of micro-aliquots of sample solutions that constitutes their main superiority over pneumatic aspiration into the flame. Continuous sample introduction has, however also been coupled with the use of heated graphite tube atomizers, but such systems suffer from serious losses of sensitivity.

Murphy, K. M., Clyburn, S. A., and Veillon, C., Anal. Chem., 45, 1468 (1973), described several furnace atomizers. The atomizers were designed for continuous introduction of the sample aerosol in argon carrier gas. However, this system has the disadvantage of a serious loss of sensitivity as a result of operation in a continuous mode. Because of the very short period of time spent by the sample in the hot environment, atomization is incomplete and only relatively poor detection limits are possible.

A sample introduction system also suited to use with flames was described by Hieftje and Malmstadt, Anal. Chem., 40, 1860 (1968). This system of sample injection introduces isolated droplets of sample solution into the flame rather than commonly used aerosol. The droplets are generated by forcing a jet of liquid from a capillary which is mechanically vibrated by a bimorph electromechanical transducer. The size of the droplets can be varied from 10 to 200 um and is determined by the vibration frequency and the diameter of the capillary. The frequency of droplet introduction, may be varied from 0.1 to $2 \times 10^5 S^{-1}$. This apparatus was primarily developed for research investigations and is not suited to general use for chemical analysis.

Existing procedures for the application of microvolumes of analyte in solution to furnaces used in atomix spectrometry require stringent control to achieve high precision for volume measurements and for reproducible sample placement. The smallest pulse-operated graphite furnace exhibits the best absolute sensitivities in comparison with its larger counterparts. When sufficient volume of sample is available, however, the small furnace has been somewhat handicapped by its inability to accept samples in excess of 5 $\mu l$ (in the tube version) without resort to use of multiple aliquots with drying between additions or application of larger volumes by syringe, with continuous drying on contact with the furnace.

We have found that the concentrational sensitivity of any pulse-operated furnace can be considerably improved by depositing the analyte in aerosol form on the internal surface areas of the furnace under controlled conditions. This approach also obviates the need for skilled application of microvolumes of analyte in solution, as used in existing systems. The invention allows aerosol deposition requiring a minimum number of operations and skills, and readily provides higher precisions than those obtained by experienced operators using existing systems.

In one aspect the present invention provides a method of deposition of an analyte sample in aerosol form under controlled conditions onto the internal surfaces of a furnace atomizer, especially for a pulse-operated furnace atomizer, comprising converting said analyte sample to aerosol form by any suitable means, passing said aerosol through separator means to remove droplets of said sample which are not required in said furnace atomizer, and conveying a predetermined quantity of the aerosol from said separator means for deposition onto the internal surfaces of said furnace atomizer.

The invention further provides apparatus for generating an analyte aerosol sample for and to introduce said sample into a furnace atomizer as used in atomic spectrometry, said apparatus comprising a nebulizer with inlet means for a nebulizing gas, a spray chamber operatively connected to said nebulizer to provide a source of analyte sample in aerosol form, separator means connected to an outlet of said spray chamber to remove droplets of said sample which are not required in said furnace atomizer, discharge means in communication with said separator means adapted to deliver a predetermined quantity of aerosol at controlled rate into said furnace atomizer.

The invention will be further described with reference to the drawings and experimental data relating to embodiments of the invention. In the drawings:

FIG. 1 shows schematically the aerosol generation system of the present invention which, as a preferred embodiment, is constructed by coupling a standard nebulizer spray chamber system from a Perkin Elmer 460 atomic absorption spectrometer to a droplet separator and thence to a suitably tapered delivery tube. The variable nebulizer is operated by air supplied through a solenoid valve controlled by a timer;

FIG. 2 illustrates the effect of drying temperature on lead atomic-absorption, using a cup-type furnace. Graphs A,B and C represent the effect of changing the delivery tube diameter from 1.5 mm to 2.0 mm to 2.5 mm, respectively;

Figure 3:
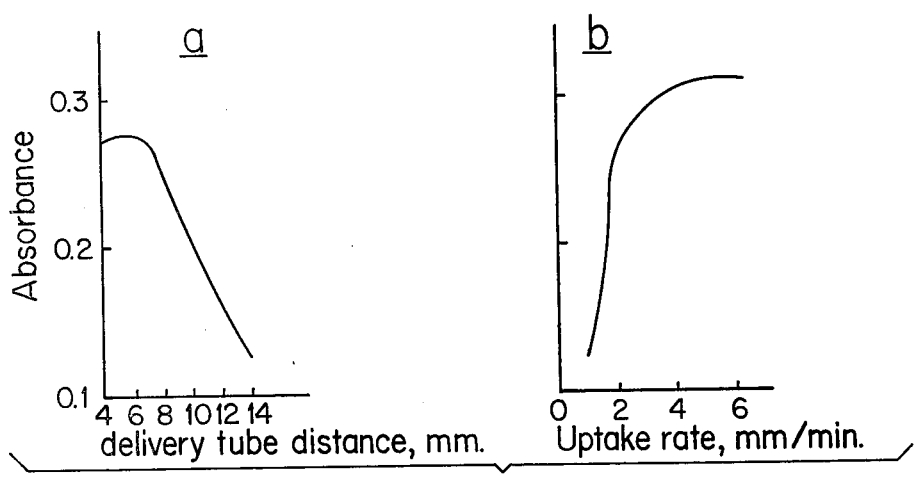
FIG. 3 illustrates the effect of (a) delivery tube position (distance of orifice from furnace wall) and (b) solution uptake rate, on lead absorbance at 283.3 nm, measured in a tubular furnace and using a delivery tube of 1.5 mm diameter.

Referring to FIG. 1, a nebulizer 1 in combination with a spray chamber 3 is connected to a droplet separator 4. The nebulizer 1, which is preferably adjustable, is connected to a nebulizing gas supply 8 through a solenoid 2 or other control valve. Regulation of deposition can be achieved through a timer operatively connected to the control valve. By timing the aerosol production the amount of analyte deposited in aerosol form inside the furnace 6 can be varied within the range from ultra-trace to macro levels. An alternative system to control the amount of analyte deposition could also employ calibrated micro-tubes for the instruction of measured volumes of solutions to the aerosol generator. The outlet of the spray chamber 3 is connected to the right-angled or elbowed entry tube 11 of the droplet separator. Aerosol droplets enter the droplet separator 4 from the spray chamber 3 via elbowed entry tube 11 and into the inverted conical chamber 9. Larger droplets or droplets of the aerosol sample that might otherwise adversely affect the performance of the apparatus if permitted to enter the delivery tube 5 or the furnace 6, are allowed to collect in the trap 10 at the lower end of the droplet separator. Acceptable aerosol droplets are allowed to enter the furnace 6 via the delivery tube 5 at a controllable or predetermined rate, by any suitable means.

The stream of sample aerosol enters the tubular furnace 6 through the sampling orifice 7, which is only 1.5 mm in diameter. If a delivery tube of comparable diameter were used, the pressure inside the system would be excessive. In order to keep the pressure within 5 mm/Hg above atmospheric pressure, a diameter of 2.5 mm was selected for the delivery-tube and the air flow-rate was maintained at 9 l/min. With this arrangement a reproducible portion of the sample aerosol was deposited on the outside of the furnace as well as the inside. When atomized, the material from the outside furnace surface is swept upwards by the protective nitrogen sheath and therefore does not contribute to the measured atomic-absorption signal. Reduced sensitivities were obtained when the aerosol stream was divided between two delivery tubes with one matching the diameter of the sampling orifice and the other vented, the total cross-sectional area of the delivery tubes being selected so that the pressure inside the system was again not more than 5 mm/Hg above the atmospheric pressure.

When the cup version of the furnace was used, the delivery tube was positioned so that the aerosol entered through the top opening. With a range of delivery tubes of 1.5-2.5 mm diameter, the total volume of the aerosol entered the cup.

With the furnace 6 clamped between supporting electrodes, the delivery tube 5 is mounted approximately 5 mm from the sampling orifice 7 or the cup opening. It is positioned centrally with respect to the sampling orifice so that the wet aerosol stream enters the furnace and collides with the opposite wall and is then deposited over a proportion of the internal areas. The quantity of analyte accumulated in the furnace is accurately controlled by timing the aerosol production by means of the solenoid valve. Alternatively, measured volumes of the analyte solution can be nebulized.

If the deposition produces takes place with no heating applied to the furnace, liquid accumulates so rapidly that within a few seconds it fills the furnace and is forced out of the ends by the air stream. When, on the other hand, the furnace is maintained at a suitable elevated temperature while the aerosol is being deposited, the wet aerosol is dried on contact with the furnace wall and the range of amounts of analyte deposited can be varied from ultra-trace to macro levels.

Ideally, the furnace temperature should remain constant while the aerosol is being deposited. Since the furnace control system used in this invention is not able to keep the furnace at a preset constant temperature, some time has to be allowed, after the initiation of the heating sequence, for the furnace to reach the operating temperature suitable for aerosol deposition. Measurements with a chromel-alumel thermocouple indicate that 15 sec is sufficient time for the furnace to reach a near constant temperature. For example, when the heating is applied for a further 5 sec, the temperature rises by only approximately 10%.

Typically, the preheating period of 15 sec is followed by aerosol deposition lasting usually between 5 and 20 sec. With air used as nebulizing gas 5-10 sec is allowed between the end of deposition and the start of ashing or atomization so that air and water vapour are removed from the furnace by the purging gas. The atomization voltage is then applied for 3 sec. Consequently the typical cycle time is 20-50 sec.

Relative standard deviations for a series of 20 measurements for lead, copper and cadmium aqueous solutions at 0.01-0.2 ppm levels and 5-sec deposition times, ranged between 0.6 and 1.4% for the tubular furnace and between 2.5 and 4.0% for the cup furnace.

The result for the tubular furnace suggests that it is indeed possible for furnace atomizers to approach the precision of flame atomization systems once the error inherent in the syringe application of small volumes has been eliminated. It is also clear that the actual process of atom production in the furnace system studied is inherently reproducible. During the experimental work however, it was observed that strong air movement, such as that caused by extractor hoods, may affect the atom population inside the furnace because of the open construction of this system. Once the furnace was located in a relatively draught-free position, the problem was eliminated.

The high precision of the tubular furnace operation may also be partly ascribed to the deposition of the aerosol in the form of a thin uniform layer rather than as a single large droplet. As matrix residues confined to limited areas can lead to reduced sensitivity, aerosol deposition should prove beneficial for work with complex matrices.

To account for the lower precision observed with the cup furnace, it has to be realized that the wet aerosol collides with the furnace wall at a velocity of approximately 30 m/sec. In the tubular furnace, the portion of the aerosol which is not deposited can leave through the 5 ends of the tube without any obstructions and is then swept upwards by the nitrogen stream. The construction of the cup version of the furnace does not allow free expansion of the aerosol stream and this is mainly responsible for the lower precision.

To establish the proportion of the nebulized analyte solution which is deposited on the furnace, 5 ml of 1000 ppm copper solution was nebulized and delivered via a 2.5 mm diameter delivery tube. The material deposited on the furnace under the previously mentioned conditions was then dissolved in distilled water and the solution analyzed by flame atomic-absorption. For the tubular furnace, 4.0% of the nebulized solution was retained on both the inside and outside of the furnace. From comparison of the copper atomic-absorption signals for the syringe and aerosol deposition of dilute solutions, the proportions of the nebulized solution deposited inside the furnace was estimated to be between 1.9 and 2.6%. These values correspond to a solution deposition rate of approximately 1 μl/sec. It is envisaged that use of a droplet generator, especially with applied electric current to control the flow of droplets, will produce a uniform stream of droplets from a vibrating capillary and into the furnace to be deposited with efficiency approaching 100%.

Experiments with a larger diameter delivery tube confirmed that the essential requirement for efficient deposition is that the aerosol should strike the furnace wall at high velocity. For example, increasing the cross-sectional area of the delivery tube by a factor of 5.8 (i.e., increasing the diameter from 2.5 to 6 mm) reduces the aerosol velocity from 30.5 to 5.3 m/sec. At the same time, the sensitivity is reduced by a factor of 47. Even when a correction is introduced for a larger proportion of the aerosol deposited on the outside of the furnace with the wider delivery tube, the reduced aerosol velocity still results in reduction by a factor of 8 in the efficiency of deposition.

The effect of drying temperature on the lead atomic-absorption signal measured with the cup version of the furnace is shown in FIG. 2. At drying temperatures below 70° the deposited aerosol was not completely dried and additional drying had to be applied before proceeding to the atomization stage. From FIG. 2 it can be seen that the efficiency of aerosol deposition rapidly declines at temperatures above 200° and at approximately 350° practically no aerosol is retained on the furnace wall. The same behaviour is observed for the tubular furnace.

The decline in the efficiency of aerosol capture can probably be explained in terms of the progressive drying of the aerosol during its passage through the furnace. As the furnace temperature increases, a larger proportion of the dry aerosol is formed and when the aerosol is dried completely before it reaches the inside wall of the furnace, none of it is retained.

FIG. 3 illustrates the variation in the lead atomic-absorption signal measured in the tubular furnace as a function of the delivery tube position and solution uptake-rate. The optimum position of the delivery tube for maximum deposition is at 5 mm from the furnace. The delivery tube is not affected by the heat radiated when atomization takes place.

The effect of the solution uptake-rate on the analytical signal is similar to the behaviour of flame systems. The efficiency of aerosol production decreases as the solution uptake rate increases and consequently only a modest improvement in sensitivity is realized by increasing the uptake rate from 2 ml/min to 4 ml/min, and there is practically no further effect on sensitivity at rates above 4 ml/min.

Figure 4:
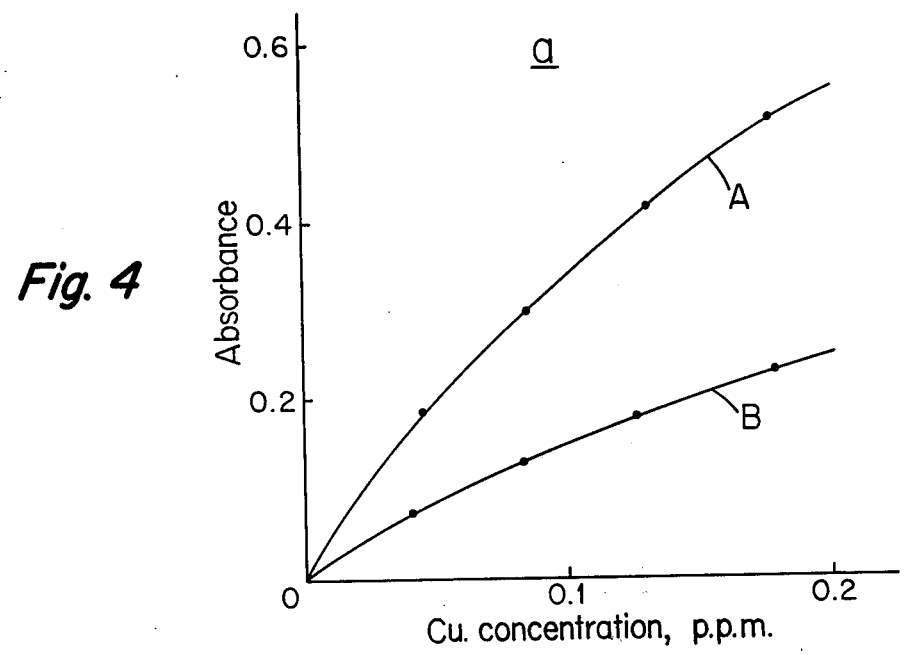
FIG. 4 illustrates calibration curves for copper measured at 324.8 nm in a tubular furnace. Graph A represents aerosol deposition over 5 seconds, and Graph B represents syringe application of 2 μl volume.

FIG. 4 shows a comparison of calibration curves obtained by use of both syringe and aerosol deposition for solutions of variable concentration. Sensitivities for these two techniques are compared in Table 1. When the experimental values shown here for syringe-deposition are compared with those for 20-sec aerosol deposition (equivalent to a volume of 20 μl), it is obvious that the increase in sensitivity is virtually linearly related to the volume of sample deposited.

TABLE I

SENSITIVITIES *FOR SYRINGE AND AEROSOL DEPOSITION

| Element | Line nm | Absolute sensitivity, pg | Concentrational sensitivity (2-μl volume), ppM+ | Concentrational sensitivity (20-sec deposition), ppM |
|---|---|---|---|---|
| Cd | 228.8 | 0.3 | 0.2 | 0.02 |
| Cu | 324.8 | 6 | 3 | 0.4 |
| Pb | 217.0 | 2 | 1 | 0.2 |
| Pb | 283.3 | 8 | 4 | 0.4 |

*For 1% absorption
+Parts per milliard ($10^9$)

Figure 5:
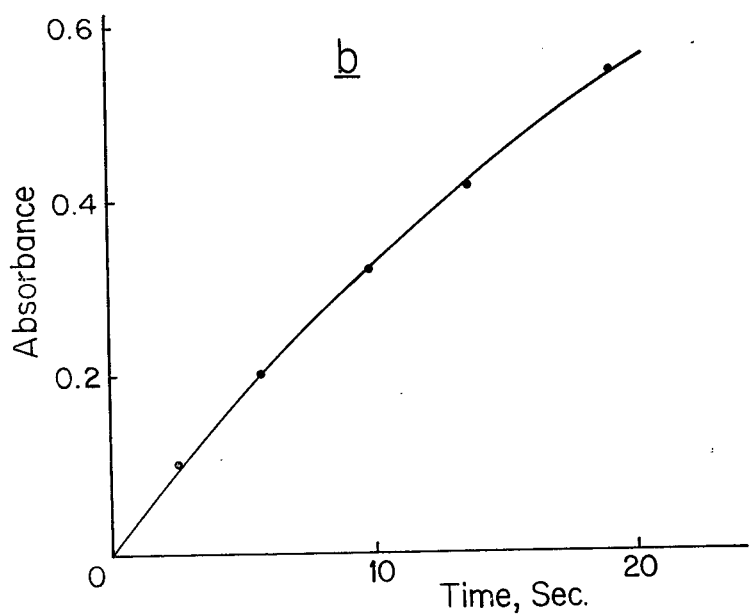
FIG. 5 demonstrates the possibility of using a single standard to construct a calibration curve by varying the aerosol deposition time.

FIG. 5 demonstrates the possibility of using a single standard to construct a calibration curve by varying the aerosol deposition time. The amount of the analyte deposited in the furnace from the aerosol and therefore the improvement in concentrational sensitivity, is restricted only by the sample volume available and the matrix concentration.

Measurements were performed with a Varian Techtron model 63 CRA furnace mounted in a Varian Techtron AA-5 atomic-absorption spectrometer. Furnaces coated with pyrolytic graphite, with the coating removed from the exterior, were used. This modification was found to result in highly reproducible furnace operation since the contacts between the furnace and the supporting electrodes were maintained in perfect order throughout the lifetime of the furnace.

Hollow-cathode lamps by the same manufacturer were used for all elements investigated and were operated at the manufacturer's recommended currents. Peak-heights were recorded with a Mace FBQ 100 chart-recorder. Drying temperatures were monitored with a chromel-alumel thermocouple inserted inside the furnace to make contact with the inside wall. The hot-junction was made very fine in order to reduce the time constant.

Although the invention has been described above with reference to preferred embodiments and drawings, it will be appreciated that numerous variations, modifications or alternatives may be substituted for specifically described features, without departing from the spirit or scope of the invention as broadly described.

We claim:

1. A method of atomizing an analyte sample including the steps of: heating a graphite tube furnace to an analyte drying temperature; converting said analyte sample to aerosol form; passing said aerosol through separator means to remove large droplets from said sample; conveying said aerosol from said separator means to delivery means through which said aerosol is deposited onto the internal surface of said furnace; ceasing said conversion of said analyte sample after a predetermined period of time to control the quantity of analyte sample deposited on said internal surface; and raising the temperature of said furnace to an atomizing temperature subsequent to completing said deposition of the analyte sample.

2. A method according to claim 1, wherein a purging gas is passed through said furnace after completion of said aerosol deposition and before the temperature of said furnace is raised.

3. A method according to claim 1, wherein said furnace is held at said raised temperature for a predetermined period of time and is then allowed to cool for commencement of a further atomizing cycle.

4. A method according to claim 1, wherein said conversion of the analyte sample includes the use of a droplet generator which is operative to convert said sample to a uniform stream of droplets.

5. A method as claimed in claim 1 wherein said analyte sample is converted to aerosol form by menas of a nebulizer-spray chamber system connected to a nebulizing gas supply via a solenoid control valve operatively connected to a timer.

6. A method as claimed in claim 1 wherein said aerosol is conveyed to said furnace so as to strike an internal wall of said furnace substantially at right angles to the path of the aerosol entering the furnace.

7. In a spectrophotometer having a hollow graphite tube furnace with an internal surface and means for periodically heating said furnace in a controlled manner, and wherein said heating means is operative during each heating period to first heat said furnace to a drying temperature and to subsequently raise the temperature of said furnace to an atomizing temperature; the improvement in the means for introducing an analyte sample to said furnace, said last-mentioned means comprising: a nebulizer having an inlet for receiving a nebulizing gas and being connected to a source of analyte sample, said nebulizer being operative to convert said analyte sample to aerosol form, timer controlled valve means operative to control supply of said nebulizer gas to said nebulizer and to thereby limit generation of said aerosol to a predetermined period of time, a spray chamber for receiving aerosol generated by said nebulizer, separator means connected to said spray chamber to receive said aerosol therefrom and being operative to remove large droplets from said aerosol, and aerosol delivery means connected to said separator means to provide an outlet for said aerosol and being aligned with an orifice in the wall of said furnace so as to deposit said aerosol on the internal surface of said furnace.

8. Apparatus as claimed in claim 7 wherein said delivery means in communication with said separator means comprises a tubular member connected to said separator, said tubular member having a tapered discharge end adjacent to but spaced from the entrance to said furnace.

9. Apparatus as claimed in claim 7 wherein said separator means comprises an entrance conduit in communication at one end with said spray chamber and at its opposite end with a main separating chamber comprising a central chamber with a droplet trap at its lower end and an opening in a wall of said central chamber at a point above said droplet trap, said opening being in communication with said delivery means.

10. Apparatus for atomizing an analyte sample including, a nebulizer having an inlet for receiving a nebulizing gas and being connected to a source of analyte sample, said nebulizer being operative to convert said analyte sample to aerosol form, timer controlled valve means operative to control supply of said nebulizer gas to said nebulizer and to thereby limit generation of said aerosol to a predetermined period of time, a spray chamber for receiving aerosol generated by said nebulizer, separator means connected to said spray chamber to receive said aerosol therefrom and being operative to remove large droplets from said aerosol, aerosol delivery means connected to said separator means to provide an outlet for said aerosol, a graphite tube furnace having an internal surface and an orifice aligned with said delivery means to provide passage for said aerosol to the internal surface of said furnace, and power means for heating said furnace.

11. Apparatus according to claim 10, wherein there is provided control means which is operative to energize said power means to cause pulsed heating of said furnace and to cause the temperature of said furnace to advance through at least two temperature steps during each heating phase, and said control means also being operative to regulate said timer-controlled valve means so that said nebulizer is operative during a period of time between said two heating steps.

12. Apparatus as claimed in claim 10 wherein said nebulizer is connectable to a source of nebulizing gas through a solenoid or other control valve with timer means operatively connected thereto to regulate deposition of analyte in said furnace.

* * * * *